(12) United States Patent
Young et al.

(10) Patent No.: US 11,369,769 B2
(45) Date of Patent: *Jun. 28, 2022

(54) DEVICE FOR PERFORMING REGIONAL ANESTHESIA

(71) Applicant: The Queen Elizabeth Hospital King's Lynn NHS Foundation Trust, Norfolk (GB)

(72) Inventors: Peter Jeffrey Young, Norfolk (GB); Joseph Joachim Carter, Norfolk (GB); Emad Eldin Fahmy Fawzy, Norfolk (GB); John Edward Gibson, Norfolk (GB)

(73) Assignee: The Queen Elizabeth Hospital King's Lynn NHS Foundation Trust, Norfolk (GB)

( * ) Notice: Subject to any disclaimer, the term of this patent is extended or adjusted under 35 U.S.C. 154(b) by 300 days.

This patent is subject to a terminal disclaimer.

(21) Appl. No.: 16/697,610

(22) Filed: Nov. 27, 2019

(65) Prior Publication Data
US 2020/0094012 A1    Mar. 26, 2020

Related U.S. Application Data

(63) Continuation of application No. 16/132,974, filed on Sep. 17, 2018, now Pat. No. 10,525,229, which is a
(Continued)

(30) Foreign Application Priority Data

Apr. 24, 2012  (GB) ........................ 1207193
Jun. 11, 2012  (GB) ........................ 1210179
(Continued)

(51) Int. Cl.
A61B 8/00     (2006.01)
A61M 19/00    (2006.01)
(Continued)

(52) U.S. Cl.
CPC ........... *A61M 19/00* (2013.01); *A61B 8/0841* (2013.01); *A61B 8/4444* (2013.01);
(Continued)

(58) Field of Classification Search
CPC ................................... A61B 8/0841
See application file for complete search history.

(56) References Cited

U.S. PATENT DOCUMENTS 3,812,855 A    5/1974  Banko
3,920,014 A   11/1975  Banko
(Continued)

FOREIGN PATENT DOCUMENTS

WO    9519142 A1    7/1995
WO    9632887 A1   10/1996
(Continued)

OTHER PUBLICATIONS

EPO, Extended European Patent Report in European Application No. 19190204.8 dated Oct. 31, 2019.

*Primary Examiner* — Joseph M Santos Rodriguez
(74) *Attorney, Agent, or Firm* — NK Patent Law (57) ABSTRACT

An anesthetic administration device comprising an infusion device, which is in fluid connection with a regional anesthetic needle by means of a feed tube. The infusion device comprises one or more anesthetic flow devices capable of triggering forward flow, and optionally backward flow, of the local anesthetic through the regional anesthetic needle. Forward, and optionally backward flow, of the local anesthetic through the regional anesthetic needle is controlled by a controller that comprises one or more actuator switches. The one or more actuator switches are positioned on the device 1 such that they may be operated by hand.

14 Claims, 5 Drawing Sheets

Related U.S. Application Data continuation of application No. 14/396,761, filed as application No. PCT/GB2013/051043 on Apr. 24, 2013, now Pat. No. 10,076,630.

(30) Foreign Application Priority Data

| | | | |
|---|---|---|---|
| Oct. 8, 2012 | (GB) | ...................................... | 1218015 |
| Nov. 14, 2012 | (GB) | ...................................... | 1220477 |

(51) Int. Cl.
| | |
|---|---|
| *A61M 5/145* | (2006.01) |
| *A61B 8/08* | (2006.01) |
| *A61M 5/158* | (2006.01) |
| *A61M 5/50* | (2006.01) |
| *A61M 5/42* | (2006.01) |
| *A61M 5/142* | (2006.01) |
| *A61M 5/31* | (2006.01) |
| *A61M 5/168* | (2006.01) |

(52) U.S. Cl.
CPC .......... *A61M 5/1452* (2013.01); *A61M 5/158* (2013.01); *A61M 5/5086* (2013.01); *A61B 8/4416* (2013.01); *A61B 8/4472* (2013.01); *A61B 8/54* (2013.01); *A61M 5/14216* (2013.01); *A61M 5/16804* (2013.01); *A61M 5/16881* (2013.01); *A61M 5/16886* (2013.01); *A61M 5/427* (2013.01); *A61M 2005/1588* (2013.01); *A61M 2005/3112* (2013.01); *A61M 2202/048* (2013.01); *A61M 2205/106* (2013.01); *A61M 2205/18* (2013.01); *A61M 2205/3334* (2013.01); *A61M 2205/3375* (2013.01); *A61M 2205/44* (2013.01); *A61M 2205/50* (2013.01); *A61M 2205/581* (2013.01); *A61M 2205/583* (2013.01)

(56) References Cited

U.S. PATENT DOCUMENTS

| | | | |
|---|---|---|---|
| 5,295,967 | A | 3/1994 | Rondelet et al. |
| 5,542,915 | A | 8/1996 | Edwards et al. |
| 5,609,573 | A | 3/1997 | Sandock |
| 5,910,135 | A | 6/1999 | Hadzic et al. |
| 5,976,110 | A | 11/1999 | Greengrass et al. |
| 6,132,414 | A | 10/2000 | Herbst et al. |
| 6,159,161 | A | 12/2000 | Hodosh |
| 6,165,188 | A | 12/2000 | Saadat et al. |
| 6,171,276 | B1 | 1/2001 | Lippe et al. |
| 7,727,224 | B2 | 6/2010 | Hadzic et al. |
| 7,806,862 | B2 | 10/2010 | Molnar |
| 8,366,672 | B1 | 2/2013 | Barton et al. |
| 8,425,474 | B2 | 4/2013 | Glassman et al. |
| 8,668,665 | B2 | 3/2014 | Gerg et al. |
| 2002/0016567 | A1* | 2/2002 | Hochman ........... A61M 5/1456 604/131 |
| 2002/0116567 | A1 | 8/2002 | Vondran, Jr. |
| 2005/0027262 | A1 | 2/2005 | Appling et al. |
| 2006/0249542 | A1 | 11/2006 | Allen |
| 2007/0233059 | A1 | 10/2007 | Christoudias |
| 2008/0103564 | A1 | 5/2008 | Burkinshaw et al. |
| 2011/0060229 | A1 | 3/2011 | Hulvershorn et al. |
| 2013/0123703 | A1 | 5/2013 | Shay |

FOREIGN PATENT DOCUMENTS

| | | | |
|---|---|---|---|
| WO | 0220073 | A2 | 3/2002 |
| WO | 2009134990 | A2 | 11/2009 |

\* cited by examiner

DEVICE FOR PERFORMING REGIONAL ANESTHESIA

CROSS-REFERENCE TO RELATED APPLICATION

This application is a continuation of, and claims the benefit of priority of, U.S. Non-Provisional patent application Ser. No. 16/132,974, titled "Device for Performing Regional Anesthesia", filed on Sep. 17, 2018, which claims the benefit of priority of, U.S. Non-Provisional patent application Ser. No. 14/396,761, titled "Device for Performing Regional Anesthesia", filed on Oct. 24, 2014, being issued as U.S. Pat. No. 10,076,630 on Sep. 18, 2018, which is a U.S. national stage application of International Patent Application No. PCT/GB2013/051043 filed on Apr. 24, 2013, which claims the benefit of GB Patent Application No. 1207193.2, filed Apr. 24, 2012, GB Patent Application N. 1210179.6, filed Jun. 11, 2012, GB Patent Application No. 1218015.4, filed Oct. 8, 2012, and GB Patent Application N. 1220477.2, filed Nov. 14, 2012, all of which are incorporated herein by reference in their entireties.

TECHNICAL FIELD

The present invention relates generally to devices for performing regional anesthesia.

BACKGROUND

Regional anesthesia is used to block the sensation in a specific part of a patient's body during and after surgery. It offers numerous advantages over conventional general anesthesia, including faster recovery time, fewer side effects, and a dramatic reduction in post-surgical pain.

In regional anesthesia, the local anesthetic is injected through a needle close to a nerve so as to block it. However, locating the nerve has often proved difficult in patients. Ultrasound is therefore used to improve the accuracy of the injection and therefore the safety of the procedure. However, a disadvantage of using an ultrasound probe is that both hands of the clinician are required to perform the block; one hand is needed to hold the regional anesthetic needle that delivers the local anesthetic, whilst the other is required to hold the ultrasound probe.

As a result, the clinician often requires assistance when carrying out the procedure. In this regard, most clinicians require an assistant to be present in order to hold the syringe connected to the needle and to inject the local anesthetic by pressing the syringe plunger at the request of the clinician. However, using an assistant has a number of disadvantages. For example, the clinician must rely on the assistant to accurately follow orders relating to the timing and speed of the injection, and also to keep an appropriate pressure exerted upon the syringe plunger.

Accordingly, there is a need in the art for a device that allows the clinician to administer the local anesthetic him or herself without the need for any assistance. This need is addressed by the present invention, which solves one or more of the above-mentioned problems.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In more detail, a first aspect of the present invention provides an anesthetic administration device including:
(a) a regional anesthetic needle;
(b) an infusion device in fluid communication with the regional anesthetic needle via a feed tube, wherein the infusion device includes one or more anesthetic flow devices capable of generating forward, and optionally backward, flow of local anesthetic through the regional anesthetic needle; and
(c) a controller that comprises one or more actuator switches, wherein the one or more actuator switches activate forward, and optionally backward, flow of the local anesthetic through the regional anesthetic needle, and wherein the one or more actuator switches are positioned on the regional anesthetic needle and/or the feed tube such that they may be operated by hand.

In another aspect, the present invention provides an anesthetic administration device including:
(a) a regional anesthetic needle;
(b) an infusion device in fluid communication with the regional anesthetic needle via a feed tube, wherein the infusion device includes one or more anesthetic flow devices capable of generating forward, and optionally backward, flow of local anesthetic through the regional anesthetic needle;
(c) an ultrasound probe; and
(d) a controller that includes one or more actuator switches, wherein the one or more actuator switches activate forward, and optionally backward, flow of the local anesthetic through the regional anesthetic needle, and wherein the one or more actuator switches are positioned on the ultrasound probe, the regional anesthetic needle and/or the feed tube such that they may be operated by hand.

DETAILED DESCRIPTIONS

As defined herein, the term "aspirate" or "aspiration" means to remove or withdraw a liquid backwards through the regional anesthetic needle. This may be achieved by generating negative pressure in the system. Aspiration allows for visual inspection of the withdrawn liquid for blood in order to ensure that the regional anesthetic needle is not injecting the local anesthetic into a blood vessel.

The term "infuse" or "infusion" means to inject or introduce a liquid forward through a needle. This may be achieved by generating positive pressure in the system.

Examples of "local anesthetic", include, but are not limited to, benoxinate, proparacaine, etidocaine, hexylcaine, mepivacaine, prilocaine, chloroprocaine, lidocaine, procaine, bupivacaine, dibucaine, ropivacaine and tetracaine, as well as their pharmaceutically acceptable salts and esters.

The infusion device may further comprise a local anesthetic reservoir for storing the local anesthetic. The local anesthetic reservoir is in fluid communication with the feed tube.

The anesthetic flow device can be any device known in the art that is capable of generating fluid flow, and therefore infusion and optionally aspiration. Non-limiting examples include pumps, for example pump mechanisms having a direct drive/screw system, a peristaltic or rotary action. In another example, the anesthetic flow device may generate fluid flow by decreasing or increasing the volume of the local anesthetic reservoir, e.g. a syringe pump and the like.

In one embodiment, the infusion device comprises a single anesthetic flow device, e.g. a single pump. In this embodiment, the anesthetic flow device is capable of triggering forward flow of the local anesthetic from the infusion device to the regional anesthetic needle via the feed tube, and optionally backward flow of the local anesthetic to the infusion device.

In another embodiment, the infusion device comprises two separate anesthetic flow devices:
  (i) a first anesthetic flow device (e.g. a first pump) capable of triggering forward flow of the local anesthetic from the infusion device to the regional anesthetic needle via the feed tube, and
  (ii) a second anesthetic flow device (e.g. a second pump) capable of triggering backward flow of fluid through the regional anesthetic needle into an aspiration tube, wherein the aspiration tube enables fluid communication between the regional anesthetic needle and the infusion device. In one embodiment, the aspiration tube and the feed tube merge so as to form a single tube prior to joining the regional anesthetic needle. In an alternative embodiment, the aspiration tube and the feed tube are separate tubes.

In one embodiment, the infusion device comprises a control unit, which may be used to set the parameters of infusion and/or aspiration. Pre-set parameters can include fluid volume limits, flow rate limits and pressure limits. Thus, the control unit may store a number of pre-programmed settings having specific infusion rates, pressures and/or fluid volumes. It may also allow the clinician to create and store a plurality of user-defined procedures.

The infusion device is typically set to function at pressures of less than about 25 psi (e.g. less than 5, 6, 7, 8, 9, 10, 11, 12, 13, 14, 15, 16, 17, 18, 19, 20, 21, 22, 23, 24 or 25 psi). In this regard, a normal injection pressure would generally be less than about 15 psi, an intermediate injection pressure would be about 15 to about 25 psi, and an abnormal pressure would generally be greater than about 25 psi. The infusion device is typically set to function at flow rates of above about 5 ml/min, e.g. from about 10 ml/min to about 300 ml/min, or from about 15 ml/min to about 50 ml/min, such as from about 20 ml/min to about 30 ml/min.

The regional anesthetic needle may be a standard, hollow hypodermic needle. It has a distal end that inserts into a patient and delivers the local anesthetic to the injection site near or proximate the target nerve of the patient. The needle also has a proximal end, which may comprise a needle hub, that is capable of accepting the feed tube, e.g., via a conventional Luer connection, and optionally also the aspiration tube, e.g., via a conventional Luer connection. The regional anesthetic needle may be disposable.

The needle can range in length, for example, it may be a one inch (1"), a two inch (2"), a three inch (3") or a four inch (4") length needle. The gauge of the needle can also vary, for example it may be 18, 19, 20, 21 or 22 gauge. The length and gauges of the needle utilized will depend on the procedure and patient. Furthermore, the needle may be echogenic which allows it to be visualized with ultrasound imaging. In addition, or in the alternative, the needle may be a stimulating needle which can be attached to a conventional nerve stimulator in order to locate the target nerve.

The ultrasound probe can be any device known in the art for emitting and detecting high frequency sound. Higher frequencies (e.g. 10-18 MHz) can be used to produce high resolution images, whereas lower frequencies can be used to scan deeper structures (e.g. 3-10 MHz).

The ultrasound probe forms part of an ultrasound imaging system, which also comprises a processing unit and an ultrasound monitor. The ultrasound probe may take a variety of different shapes and sizes.

In one embodiment, the ultrasound probe comprises a transducer having one or more piezoelectric crystals that are capable of sending pulses of sound into the body and of detecting the resulting echo. When an electric current is applied to the piezoelectric crystals, a sound wave is produced that travels outward from the probe into the body. As the sound passes through tissues it is either absorbed, reflected or allowed to pass through, depending on the density of the tissue. When the sound wave is reflected back to the probe, it causes the piezoelectric crystals to emit an electrical current that can be processed by the processing unit to form an image that is normally displayed on the ultrasound monitor. This allows the clinician to simultaneously visualise the target nerve and its surrounding structures, thereby allowing the safe administration of the local anesthetic.

In operation, the clinician can control the forward or backward flow of the local anesthetic through the regional anesthetic needle by means of the controller. The controller comprises one or more actuator switches operable by hand that are capable of activating infusion and optionally aspiration of the local anesthetic, thereby allowing the clinician to administer the local anesthetic without the need for any assistance.

In one embodiment, the actuator switch operates in two positions. In this regard, the first position may activate infusion, i.e. forward flow of the local anesthetic through the needle, and the second position may activate aspiration, i.e. backwards flow of the local anesthetic through the needle. Alternatively, the second position may halt flow of the local anesthetic through the needle. In this latter embodiment, aspiration may occur intermittently on an automatic basis.

In another embodiment, the actuator switch operates in three positions, the first position activates infusion, the second position activates aspiration, and the third position halts flow of the local anesthetic through the needle.

The clinician can control flow of the local anesthetic by moving the actuator switch to the appropriate position.

In a further embodiment, the controller comprises two actuator switches, wherein the first actuator switch activates infusion, and the second actuator switch activates aspiration.

The one or more actuator switches may be any suitable switch known in the art, for example it may be a pushbutton switch, a toggle switch, a rocker switch, a slide switch, or the like.

In one embodiment, the actuator switch is a pushbutton switch that can be in at least two positions, e.g. two or three positions, such as a raised or depressed position and optionally an intermediate position. In one example, the depressed position may activate forward flow of the local anesthetic through the needle, and the raised position may activate backwards flow of the local anesthetic through the needle, and optionally the intermediate position may halt flow of the local anesthetic through the needle. All permutations, however, are envisaged. The pushbutton switch may be biased in the position that halts flow of the local anesthetic through the needle.

In a further embodiment, the pushbutton switch comprises two pushbutton switches, whereby depression of the first pushbutton switch activates forward flow of the local anesthetic through the needle, and depression of the second pushbutton switch activates backwards flow of the local anesthetic through the needle. Both pushbutton switches may be biased in the raised position so as to halt flow of the local anesthetic through the needle. Alternatively, the two pushbutton switches may alternate between the raised and depressed position, such that depression of the raised pushbutton switch automatically raises the depressed pushbutton switch.

In another embodiment, the actuator switch is a rocker switch that rocks along a centre axis between at least two positions e.g. two or three positions, such as a first position that activates infusion, a second position that activates aspiration, and optionally a third position that halts flow of the local anesthetic through the needle. All permutations, however, are envisaged. The rocker switch may be biased in the position that halts flow of the local anesthetic through the needle. In a further embodiment, the rocker switch comprises two rocker switches, whereby the first rocker switch activates forward flow of the local anesthetic through the needle, and the second rocker switch activates backwards flow of the local anesthetic through the needle. Both rocker switches may be biased in a position that halts flow of the local anesthetic through the needle.

In yet another embodiment, the actuator switch is a toggle switch that pivots through an arc at its base between at least two positions e.g. two or three positions, such as a first position that activates infusion, a second position that activates aspiration, and optionally a third position that halts flow of the local anesthetic through the needle. All permutations, however, are envisaged. The toggle switch may be biased in the position that halts flow of the local anesthetic through the needle. In a further embodiment, the toggle switch comprises two toggle switches, whereby the first toggle switch activates forward flow of the local anesthetic through the needle, and the second toggle switch activates backwards flow of the local anesthetic through the needle. Both toggle switches may be biased in a position that halts flow of the local anesthetic through the needle.

In yet a further embodiment, the actuator switch is a slide switch that can slide between at least two positions e.g. two or three positions, such as a first position that activates infusion, a second position that activates aspiration, and optionally a third position that halts flow of the local anesthetic through the needle. All permutations, however, are envisaged. The slide switch may be biased in the position that halts flow of the local anesthetic through the needle. In a further embodiment, the slide switch comprises two slide switches, whereby the first slide switch activates forward flow of the local anesthetic through the needle, and the second slide switch activates backwards flow of the local anesthetic through the needle. Both slide switches may be biased in a position that halts flow of the local anesthetic through the needle.

In one embodiment, the one or more actuator switches are capable of controlling the flow rate and/or pressure of the local anesthetic through the needle. For example, in the case of the pushbutton switch, the flow rate and/or pressure can vary linearly with the amount of depression of the pushbutton switch. In the case of the slide switch, the flow rate and/or pressure can vary linearly with the distance that the slide switch is moved.

In another embodiment, the one or more actuator switches simply activates flow of the local anesthetic at a flow rate and/or pressure that have been preselected by the clinician, e.g. using the control panel.

The one or more actuator switches are positioned so that they may be operated by the hand of the clinician whilst she or he is holding the regional anesthetic needle and optionally the ultrasound probe. Thus, in one embodiment, the one or more actuator switches are positioned on the regional anesthetic needle, e.g. on the needle hub. In another embodiment, the one or more actuator switches are positioned on the feed tube. In yet another embodiment, the one or more actuator switches are positioned on the ultrasound probe.

In embodiments where there are a plurality of actuator switches, the actuator switches may be positioned on the same component of the anesthetic administration device (i.e. the regional anesthetic needle, the feed tube or the ultrasound probe), or on different components of the anesthetic administration device.

Actuator switches on different components may share the same function. For example, actuator switches on the regional anesthetic needle, e.g. on the needle hub, the feed tube and the ultrasound probe may all activate infusion. Alternatively, actuator switches on different components may have different functions. For example, an actuator switch on the regional anesthetic needle, e.g. on the needle hub, may e.g. activate infusion, whereas an actuator switch on the ultrasound probe may e.g. activate aspiration.

In one embodiment, the actuator switch is a stand-alone unit. In this embodiment, the actuator switch is constructed separately from the regional anesthetic needle (e.g. the needle hub), the feed tube and the ultra-sound probe. The actuator switch may be permanently or removably attached to the regional anesthetic needle, the feed tube or the ultra-sound probe by any suitable means known to the skilled person, such as an adhesive or conventional fastening means, e.g. a clip. The actuator switch may be disposable.

In another embodiment, the actuator switch forms an integral part of the regional anesthetic needle (e.g. the needle hub), the feed tube, or the ultrasound probe.

In one embodiment, the actuator switch is conFIG.d to trigger infusion and optionally aspiration by activating the one or more anesthetic flow devices. In this regard, the actuator switch may activate the one or more anesthetic flow devices by wired means, such as electric wire, or by wireless means, such as RF, IR, and BLUETOOTH®.

Thus, in use, the clinician can move the actuator switch to e.g. a position that activates infusion, thereby generating a signal that causes the anesthetic flow device to trigger forward flow of the local anesthetic from the infusion device to the regional anesthetic needle. Alternatively, the clinician can move the actuator switch to e.g. a position that activates aspiration, thereby generating a signal that causes the anesthetic flow device to trigger backward flow of the local anesthetic through the regional anesthetic needle.

In a more specific embodiment, the clinician can move the actuator switch to e.g. a position that activates infusion, thereby generating a signal that causes the first anesthetic flow device to trigger forward flow of the local anesthetic from the infusion device to the regional anesthetic needle. Alternatively, the clinician can move the actuator switch to e.g. a position that activates aspiration, thereby generating a signal that causes the second anesthetic flow device to trigger backward flow of the local anesthetic through the regional anesthetic needle into the aspiration tube.

In another embodiment, the actuator switch is conFIG.d to control flow of local anesthetic through the regional anesthetic needle by controlling one or more valves. In this embodiment, the one or more anesthetic flow devices may be set to generate a constant pressure, such as between 3-10 psi.

The one or more valves may be positioned in the feed tube and/or in the regional anesthetic needle (e.g. the needle hub) and optionally in the aspiration tube. The one or more valves can be any valve known in the art that is capable of regulating fluid control. For example, the one or more valves may comprise a valve body having an inlet port through which the local anesthetic may enter the valve body, an outlet port through which the local anesthetic may exit the valve body and an open/close mechanism by means of which flow through said inlet port and/or outlet port is controllable.

Alternatively, the one or more valves may be multi-way valves. For example, the one or more valves may comprise comprises a valve body having a first inlet port, a second inlet port, and an outlet port. An open/close mechanism is formed having the requisite channels for communicating the first inlet port with the outlet port, the second inlet port with the outlet port, and optionally for sealing the outlet.

The actuator switch may operate the open/close mechanism by electronic means, such as wired or wireless means, or by mechanical means, e.g. the valve may be a pushbutton valve.

Thus, in use, the clinician can move the actuator switch to e.g. a position that activates infusion, which in turn opens a first valve, and therefore allows the local anesthetic to flow from the infusion device to the regional anesthetic needle via the feed tube. Alternatively, the clinician can move the actuator switch to e.g. a position that halts flow of the local anesthetic through the needle, which in turn will cause a first valve to close. In a further embodiment, the clinician can move the actuator switch to e.g. a position that activates aspiration, which in turn opens a second valve, and therefore allows the local anesthetic to flow backwards out of the regional anesthetic needle into the aspiration tube. Forward flow may be generated by the first anesthetic flow device and backward flow may be generated by the second anesthetic flow device.

In another embodiment, the clinician can move the actuator switch to e.g. a position that activates infusion, thereby moving a multi-way valve so as to allow the local anesthetic to flow from the infusion device to the regional anesthetic needle via the feed tube. Alternatively, the clinician can move the actuator switch to e.g. a position that activates aspiration, thereby moving the multi-way valve so as to allow the local anesthetic to flow from the regional anesthetic needle into the aspiration tube. Forward flow may be generated by the first anesthetic flow device and backward flow may be generated by second anesthetic flow device.

Typically, the device is able to monitor the pressure and/or flow rate of the local anesthetic. It may therefore comprise a pressure sensor and/or flow rate monitor. The device may comprise visual indicators of the pressure and/or flow rate in order to assist the clinician. These may be placed on the infusion device, the regional anesthetic syringe and/or the feed tube. Examples of visual indicators include mechanical pressure gauges, and digital/LED readouts. In addition, or in the alternative, the device may emit audio indicators (e.g. changes in sound, pitch and frequency) of the pressure and/or flow rate in order to assist the clinician. For example, different sounds may be emitted to distinguish between forward and reverse flow. Moreover, changes in pitch or changes in frequency of sound may signal changes in pressure and/or flow rate.

In one embodiment, the pressure sensor monitors the pressure of the fluid in the infusion device, the feed tube and/or regional anesthetic needle and produces a corresponding pressure signal. A microprocessor compares the pressure signal to one of several thresholds in the system, and actuates an alarm whenever the selected threshold is exceeded. The alarm may be visual or audible. In addition, or in the alternative, the infusion device can be programmed to slow, stop or prevent infusion whenever the selected threshold is exceeded. Although the threshold may be set at any level, it is generally preferred that it be set at a level at or near the abnormal pressure range (e.g. about 5, 6, 7, 8, 9, 10, 11, 12, 13, 14, 15, 16, 17, 18, 19, 20, 21, 22, 23, 24 or 25 psi).

The controller can also provide some feedback (e.g. visual or tactile) to the user whenever the selected threshold is exceeded. For example, the device may prevent the actuator switch from being moved to e.g. a position that activates infusion whenever the selected threshold is exceeded.

In a further aspect, the present invention provides an anesthetic administration kit comprising:
  (a) the regional anesthetic needle as defined hereinbefore;
  (b) the infusion device as defined hereinbefore; and
  (c) the feed tube as defined hereinbefore.

In another aspect, the present invention provides an anesthetic administration kit comprising:
  (a) the regional anesthetic needle as defined hereinbefore;
  (b) the infusion device as defined hereinbefore;
  (c) the feed tube as defined hereinbefore; and
  (d) the ultrasound probe as defined hereinbefore.

The invention will now be described, by way of example only, with reference to FIGS. 1-5, which show various embodiments of the invention.

Figure 1:
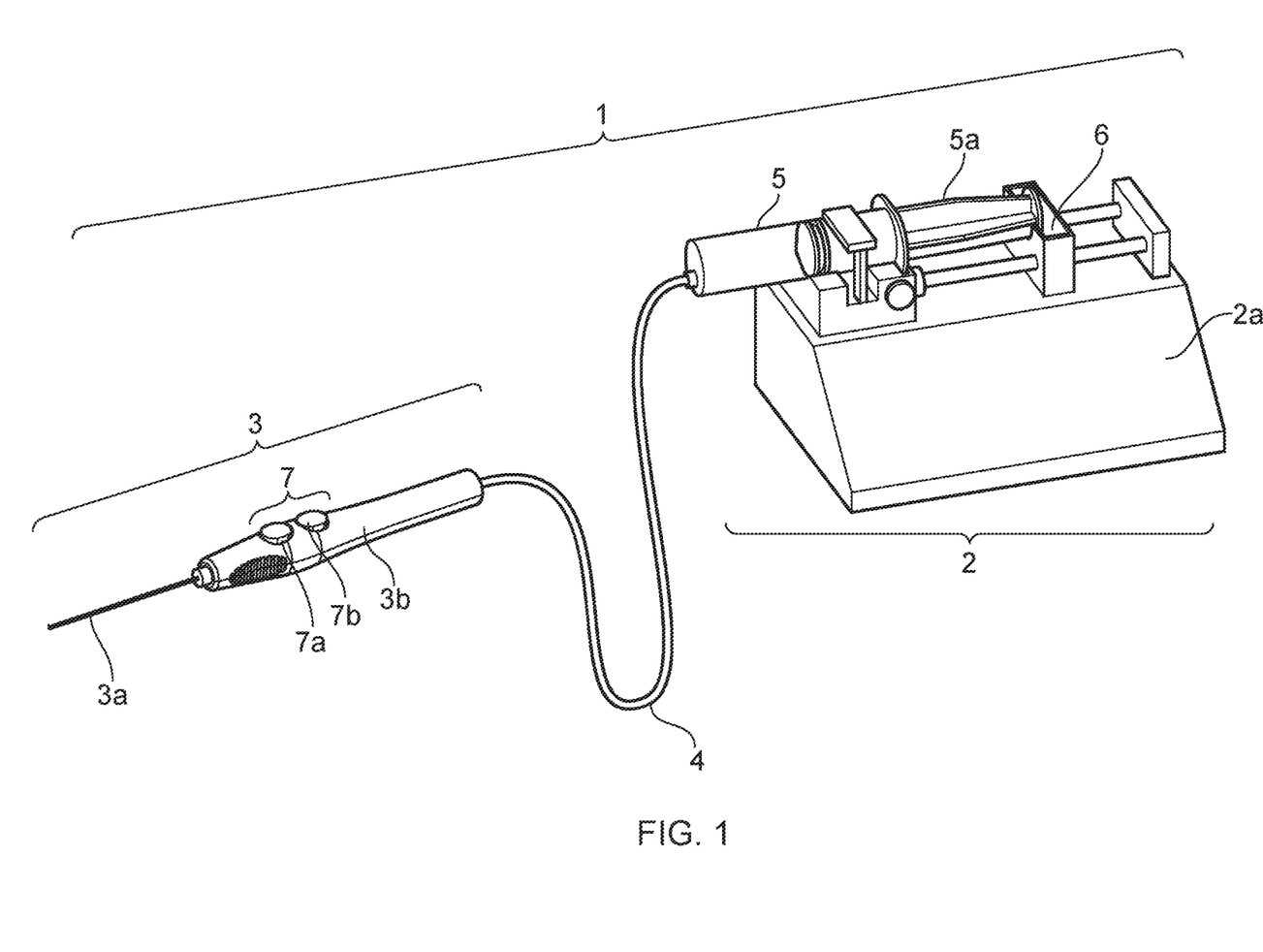
FIG. 1 shows an anesthetic administration device that enables a clinician to perform anesthesia.

FIG. 1 shows an anesthetic administration device 1 that enables the clinician to perform regional anesthesia without any additional assistance. The anesthetic administration device 1 generally comprises an infusion device 2, which is in fluid connection with a regional anesthetic needle 3 by means of a feed tube 4.

The regional anesthetic needle 3 has a distal end that is a standard, hollow hypodermic needle 3a that inserts into a patient, and also a proximal end that comprises a needle hub 3b. The length and gauge of the hypodermic needle 3a will depend on the procedure and patient. The feed tube 4 is removably secured to the needle hub 3b via a Luer connection.

The infusion device 2 comprises a housing 2a that holds a syringe 5, which acts as a local anesthetic reservoir. The plunger of the syringe 5a is controlled by a motor 6, which depresses or retracts the plunger 5a, thereby allowing it to act as an anesthetic flow device. When the plunger 5a is depressed by the motor 6, the local anesthetic is forced out of the syringe 5, through the feed tube 4 and into the regional anesthetic needle 3 so that it may be injected into the patient. The process is reversed when the plunger 5a is withdrawn by the motor 6. The delivery rate of the syringe pump 5 can be readily adjusted.

The controller 7 is positioned on the needle hub 3b. It comprises two pushbutton switches 7a 7b that can each be in a raised or depressed position. In this embodiment, the pushbuttons 7a 7b are biased in the raised position. Depression of the first pushbutton switch 7a sends a wireless control signal to the infusion device 2 which triggers the motor 6 to depress the plunger 5*a*. Depression of the second pushbutton 7*b* switch sends a wireless control signal to the infusion device 2 which triggers the motor 6 to retract the plunger 5*a*.

In order to prepare the device 1 for infusion, the syringe 5 is filled with local anesthetic and the plunger 5*a* is fully retracted. The first pushbutton switch 7*a* is then depressed until the first drop of liquid is observed on the tip of the hypodermic needle 3*a*. The first pushbutton switch 7*a* is then released.

In use, the clinician can control the flow of the local anesthetic through the regional anesthetic needle 3 by simply pressing on the pushbutton switches 7*a* 7*b*. Infusion can be activated by depressing the first pushbutton 7*a* so as to deliver the local anesthetic to the intended destination. Aspiration can be activated by depressing the second pushbutton 7*b* so as to allow for visual inspection of the withdrawn liquid in order to prevent accidental intravenous injection of the local anesthetic. The flow rate and/or pressure can vary linearly with the amount of depression of the pushbutton switches 7*a* 7*b*. Alternatively, the pushbutton switches 7*a* 7*b* simply activate flow of the local anesthetic at a flow rate and/or pressure that have been preselected by the clinician.

Figure 2:
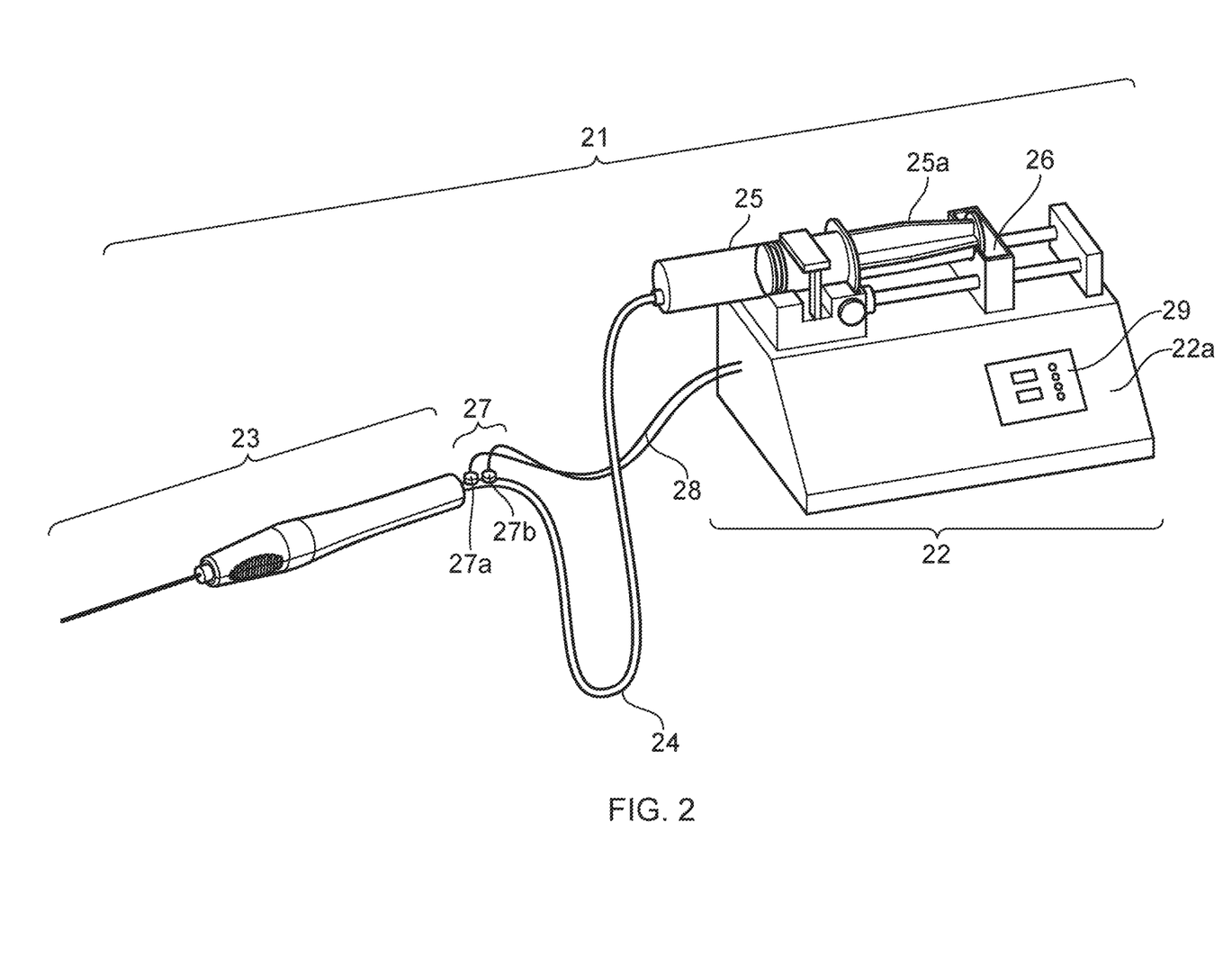
FIG. 2 shows an anesthetic administration device according to another embodiment.

FIG. 2 shows another embodiment of the invention. As in FIG. 1, the anesthetic administration device 21 generally comprises an infusion device 22, which is in fluid connection with the regional anesthetic needle 23 by means of a feed tube 24.

The infusion device 22 comprises a housing 22*a* that holds a syringe 25, which acts as a local anesthetic reservoir. The plunger of the syringe 25*a* is controlled by a motor 26, which depresses or retracts the plunger 25*a*, thereby allowing it to act as an anesthetic flow device.

In this illustrated embodiment, the controller 27 is positioned on the feed tube 24. It comprises two pushbutton switches 27*a* 27*b* that can each be in a raised or depressed position. The pushbuttons 27*a* 27*b* are biased in the raised position. The controller functions 27 via a coupling cable 28, which leads from the pushbuttons 27*a* 27*b* to the infusion device 22, and transmits and receives control signals to and from the infusion device 22.

Depression of the first pushbutton switch 27*a* sends a control signal through the coupling cable 28 to the infusion device 22 which triggers the motor 26 to depress the plunger 25*a*. Depression of the second pushbutton 27*b* switch sends a control signal through the coupling cable 28 to the infusion device 22 which triggers the motor 26 to retract the plunger 25*b*.

Also in this illustrated embodiment, the infusion device 22 comprises a control unit 29, which may be used to set the parameters of infusion and/or aspiration, e.g. flow rate and/or pressure of the local anesthetic through the needle.

Figure 3:
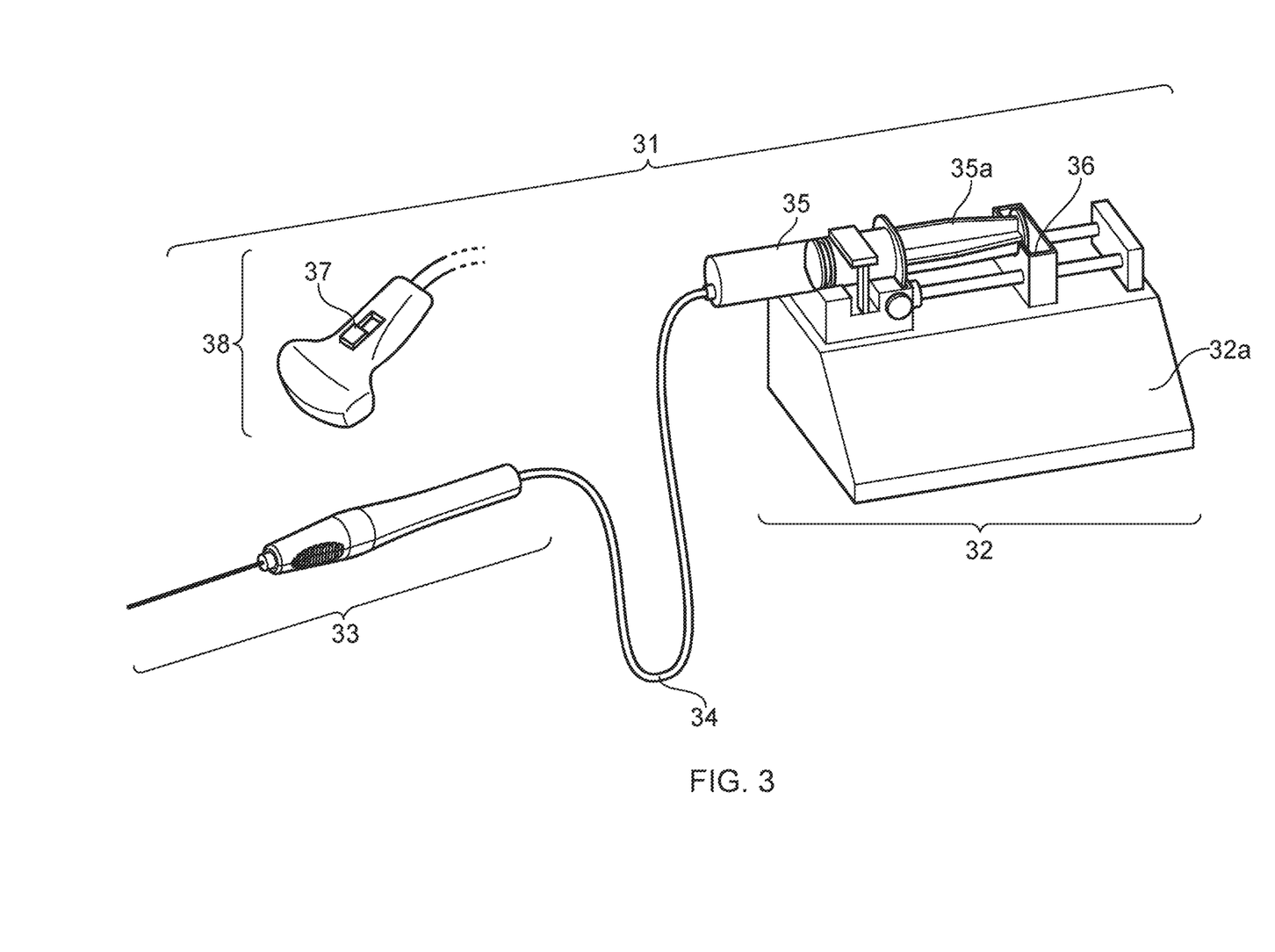
FIG. 3 shows an anesthetic administration device according to another embodiment.

FIG. 3 shows another embodiment of the invention. As in FIG. 1, the anesthetic administration device 31 generally comprises an infusion device 32, which is in fluid connection with the regional anesthetic needle 33 by means of a feed tube 34. In this embodiment, the anesthetic administration device 31 further comprises an ultrasound probe 38.

The infusion device 32 comprises a housing 32*a* that holds a syringe 35, which acts as a local anesthetic reservoir. The plunger of the syringe 35*a* is controlled by a motor 36, which depresses or retracts the plunger 35*a*, thereby allowing it to act as an anesthetic flow device.

In this illustrated embodiment, the controller 37 is positioned on the ultrasound probe 38. It comprises a slide switch 37 that can that can slide between two positions. Sliding the switch 37 to the first position sends a wireless control signal to the infusion device 32 which triggers the motor 36 to depress the plunger 35*b*. Sliding the switch 37 to the second position sends a wireless control signal to the infusion device 32 which triggers the motor 36 to retract the plunger 35*b*. The flow rate and/or pressure can vary linearly with the distance that the slide switch is moved. Alternatively, the slide switch 37 simply activates flow of the local anesthetic at a flow rate and/or pressure that have been preselected by the clinician.

Figure 4:
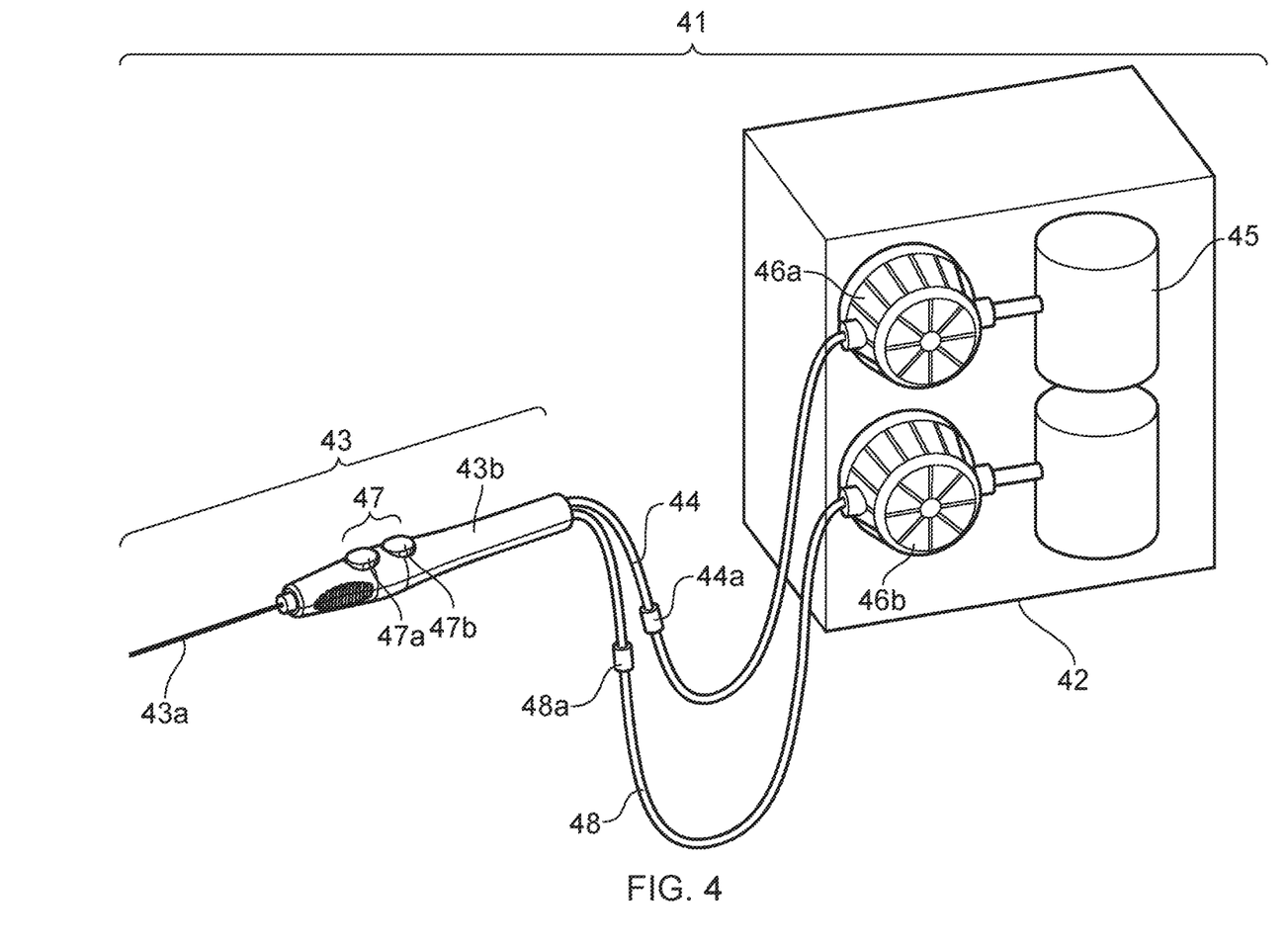
FIG. 4 shows an anesthetic administration device according to another embodiment.

FIG. 4 shows another embodiment of the anesthetic administration device 41. The anesthetic administration device 41 generally comprises an infusion device 42 in fluid connection with a regional anesthetic needle 43 by means of a feed tube 44 and an aspiration tube 48. The feed tube 44 and aspiration tube 48 comprise a first valve 44*a* and a second valve 48*a*, respectively, that controls local anesthetic flow through each tube. The feed tube 44 and the aspiration tube 48 are removably secured to the needle hub 43*b* via a Luer connection.

The infusion device 42 comprises a housing that holds a local anesthetic reservoir 45 that is in fluid connection with the feed tube 44. A first pump 46*a* draws the local anesthetic out of the reservoir 45, through the feed tube 44 and into the regional anesthetic needle 43 so that it may be injected into the patient. The infusion device 42 further device comprises a second pump 46*b* that draws the local anesthetic out of the regional anesthetic needle 43 into the aspiration tube 48.

The controller 47 is positioned on the needle hub 43*b*. It comprises two pushbutton switches 47*a* 47*b* that can each be in a raised or depressed position. In this embodiment, the pushbuttons 47*a* 47*b* are biased in the raised position. Depression of the first pushbutton switch 47*a* sends a wireless control signal to the first valve 44*a* in the feed tube 44, causing it to move to an open position, thereby allowing the local anesthetic to flow from the feed tube 44 into the regional anesthetic needle 43. Depression of the second pushbutton switch 47*b* sends a wireless control signal to the second valve 48*a* in the aspiration tube 48, causing it to move to an open position, thereby allowing the local anesthetic to flow backwards out of the regional anesthetic needle 43 into the aspiration tube 48.

In use, the clinician can control the flow of the local anesthetic through the hypodermic needle 43*a* by simply pressing on the pushbutton switches 47*a* 47*b*. Infusion can be activated by depressing the first pushbutton 47*a* so as to open the first valve 44*a* and deliver the local anesthetic to the intended destination. Aspiration can be activated by depressing the second pushbutton 47*b* so as to open the second valve 48*a* and allow for visual inspection of the withdrawn liquid in order to prevent accidental intravenous injection of the local anesthetic. The flow rate and/or pressure can vary linearly with the amount of depression of the pushbutton switches 47*a* 47*b*. Alternatively, the pushbutton switches 47*a* 47*b* simply activate flow of the local anesthetic at a flow rate and/or pressure that have been preselected by the clinician.

Figure 5:
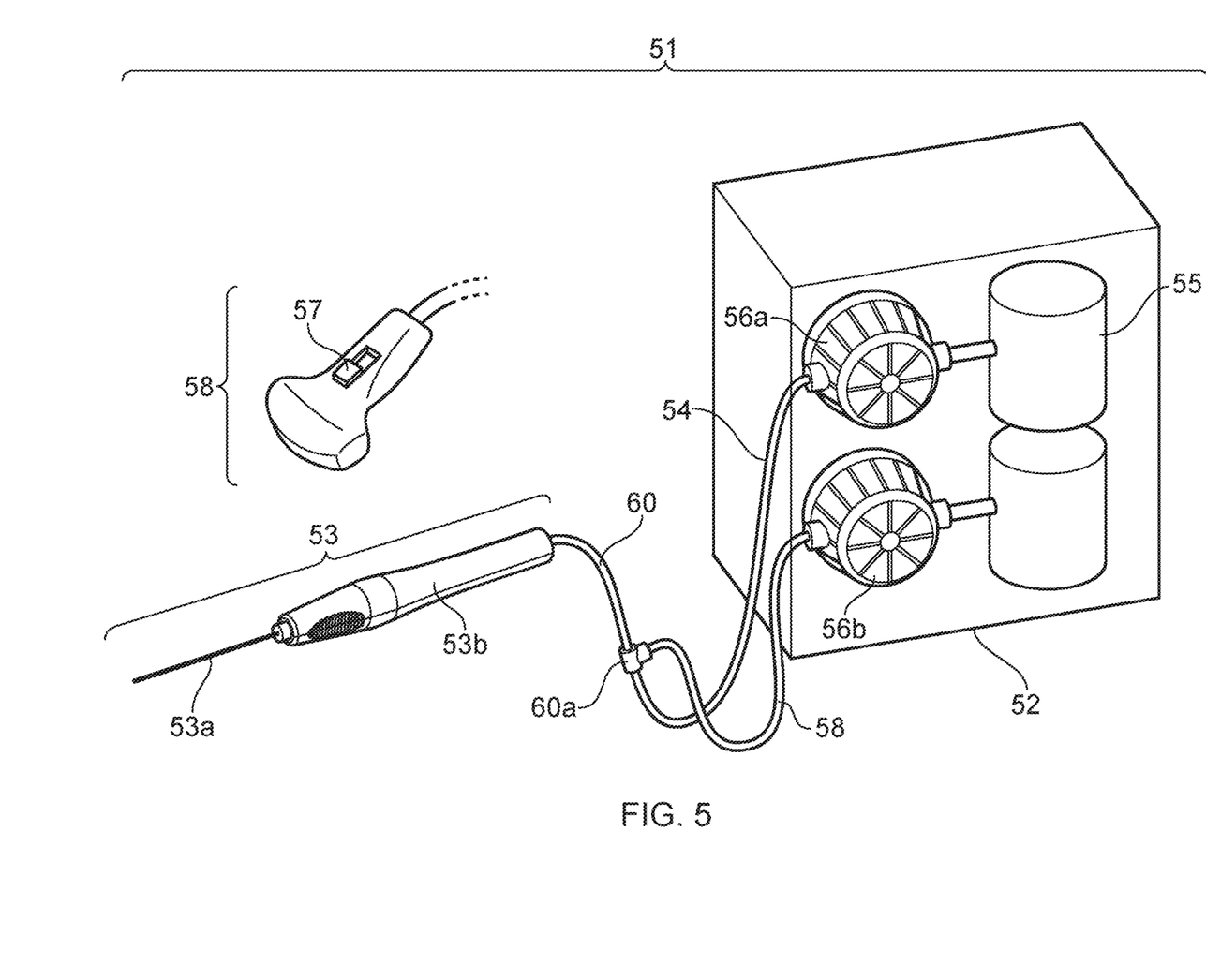
FIG. 5 shows an anesthetic administration device according to another embodiment.

FIG. 5 shows another embodiment of the anesthetic administration device 51. As in FIG. 4, the anesthetic administration device 51 generally comprises an infusion device 52 in fluid connection with a regional anesthetic needle 53 by means of a feed tube 54 and an aspiration tube 58. The feed tube 54 and aspiration tube 58 merge to form a single tube 60 that is removably secured to the needle hub 53*b* via a Luer connection. A multi-way valve 60*a* joins the feed tube 54 and the aspiration tube 58. In this embodiment, the anesthetic administration device 51 further comprises an ultrasound probe 59.

The infusion device 52 comprises a housing that holds a local anesthetic reservoir 55 that is in fluid connection with the feed tube 54. A first pump 56a draws the local anesthetic out of the reservoir 55, through the feed tube 54 and into the hypodermic needle 53a so that it may be injected into the patient. The infusion device 52 further device comprises a second pump 56b that draws the local anesthetic out of the regional anesthetic needle 53 into the aspiration tube 58.

In this illustrated embodiment, the controller 57 is positioned on the ultrasound probe 59. It comprises a slide switch 57 that can that can slide between two positions. Sliding the switch 57 to the first position sends a wireless control signal to the multi-way valve 60a, causing it to move to a position that allows the local anesthetic to flow from the feed tube 54 into the regional anesthetic needle 53 and prevents the local anesthetic from flowing into the aspiration tube 58 from the regional anesthetic needle 53. Sliding the switch 57 to the second position sends a wireless control signal to the multi-way valve 60a, causing it to move to a position that allows the local anesthetic to flow from the regional anesthetic needle 53 into the aspiration tube 58 and prevents the local anesthetic from flowing into the regional anesthetic needle 53 from the feed tube 54.

What is claimed is:

1. An anesthetic administration device comprising:
   (a) a regional anesthetic needle;
   (b) an infusion device in fluid communication with the regional anesthetic needle via a feed tube, wherein the infusion device comprises one or more anesthetic flow devices capable of generating forward flow of local anesthetic through the regional anesthetic needle; and
   (c) a controller that comprises at least one actuator switch, wherein the at least one actuator switch activates forward flow of the local anesthetic through the regional anesthetic needle, wherein the at least one actuator switch is a stand-alone unit that is constructed separately from the regional anesthetic needle and feed-tube, and wherein the at least one actuator switch is operable by hand, wherein the at least one actuator switch is selected from the group consisting of: (i) one or more pushbutton switches, wherein an amount of depression of the pushbutton switch correlates with at least one of flow rate and pressure of the local anesthetic through the regional anesthetic needle; and (ii) one or more slide switches, wherein a distance that the slide switch is moved correlates with at least one of flow rate and pressure of the local anesthetic through the regional anesthetic needle.

2. The anesthetic administration device of claim 1, wherein the infusion device further comprises an ultrasound probe.

3. The anesthetic administration device of claim 1, wherein the infusion device further comprises a local anesthetic reservoir for storing the local anesthetic, and wherein the local anesthetic reservoir is in fluid communication with the feed tube.

4. The anesthetic administration device of claim 1, wherein the infusion device comprises a single anesthetic flow device.

5. The anesthetic administration device of claim 1, wherein the infusion device comprises:
   (i) a first anesthetic flow device capable of triggering forward flow of the local anesthetic from the infusion device to the regional anesthetic needle via the feed tube, and
   (ii) a second anesthetic flow device capable of triggering backward flow of fluid through the regional anesthetic needle into an aspiration tube.

6. The anesthetic administration device of claim 1, wherein the anesthetic flow device is a pump.

7. The anesthetic administration device of claim 1, wherein the regional anesthetic needle comprises a hypodermic needle and a needle hub.

8. The anesthetic administration device of claim 1, wherein the at least one actuator switch operates in a first position that activates forward flow of the local anesthetic through the regional anesthetic needle, and a second position that activates backward flow of the local anesthetic through the regional anesthetic needle.

9. The anesthetic administration device of claim 1, wherein the at least one actuator switch operates in a first position that activates forward flow of the local anesthetic through the regional anesthetic needle, a second position that activates backward flow of the local anesthetic through the regional anesthetic needle, and a third position that halts flow of the local anesthetic through the regional anesthetic needle.

10. The anesthetic administration device of claim 1, wherein the controller comprises two actuator switches, wherein the first actuator switch is capable of activating forward flow of the local anesthetic through the regional anesthetic needle, and the second actuator switch is capable of activating backward flow of the local anesthetic through the regional anesthetic needle.

11. The anesthetic administration device of claim 1, wherein the anesthetic administration device comprises at least one of a flow rate monitor and a pressure sensor capable of monitoring the pressure of the local anesthetic.

12. The anesthetic administration device of claim 11, wherein the pressure sensor, flow rate monitor, or both comprise a visual indicator, audio indicator, or both of the pressure, flow rate, or both pressure and flow rate.

13. The anesthetic administration device of claim 12, wherein the pressure sensor (i) actuates at least one of a visual and audio alarm when a pressure threshold is exceeded; and (ii) causes infusion to slow or stop when a pressure threshold is exceeded.

14. The anesthetic administration device of claim 1 or claim 2, wherein the at least one actuator switch is capable of being removably attached to the regional anesthetic needle, the feed tube or the ultra-sound probe.

* * * * *